United States Patent [19]
Velvart et al.

[11] Patent Number: 5,219,284
[45] Date of Patent: Jun. 15, 1993

[54] SET OF INSTRUMENTS FOR REAMING OUT DENTAL ROOT CANALS

[75] Inventors: Peter Velvart, Birmensdorf; Jean-Claude Randin, Ballaigues, both of Switzerland

[73] Assignee: Les Fils D'Auguste Maillefer, Societe Anonyme A Ballaigues, Switzerland

[21] Appl. No.: 837,162

[22] Filed: Feb. 18, 1992

[30] Foreign Application Priority Data

Mar. 1, 1991 [CH] Switzerland ............................ 621/91

[51] Int. Cl.$^5$ ................................................ A61C 5/02
[52] U.S. Cl. ................................................ 433/102
[58] Field of Search ........................... 435/102, 224

[56]  References Cited

U.S. PATENT DOCUMENTS

| 4,332,561 | 6/1982 | McSpadden | 433/102 |
| 4,518,356 | 5/1985 | Green . | |
| 4,971,556 | 11/1990 | Ritano | 433/102 |
| 5,017,138 | 5/1991 | Schilder | 433/102 |
| 5,026,284 | 6/1991 | Martin | 433/102 |

Primary Examiner—Robert P. Swiatek
Assistant Examiner—Nicholas D. Lucchesi
Attorney, Agent, or Firm—Silverman, Cass & Singer, Ltd.

[57] ABSTRACT

A set of instruments is provided for reaming out dental root canals. The instruments of the set are distributed in groups of three having, in each group, a common diameter D1 measured at the root of its terminal point. In each group, the diameter D2 measured at the root of the cutting lips of a conical stem of the instrument is different, from one instrument to the next one of the group. Thus, the conicity of the three instruments of each group increases from one to the next, which enables a practitioner to ream out dental root canals to impart thereto a more wide-mouthed shape than is usually the case, such shape being especially suitable to be sealed by means of gutta-percha.

2 Claims, 2 Drawing Sheets

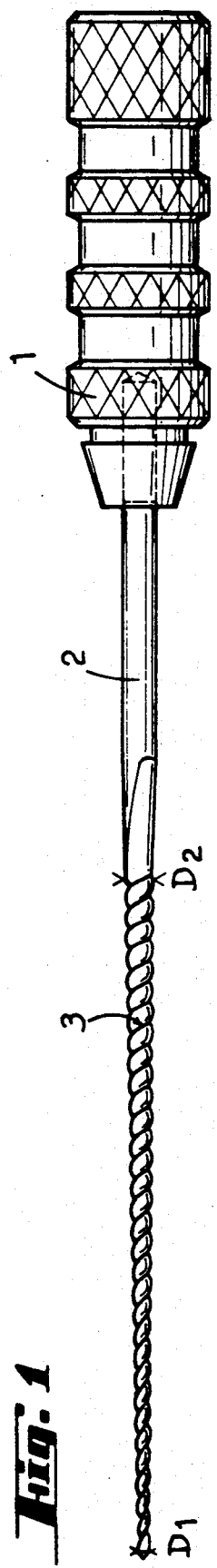
Fig. 1
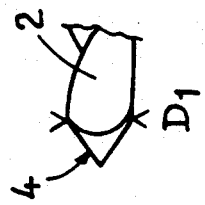
Fig. 2
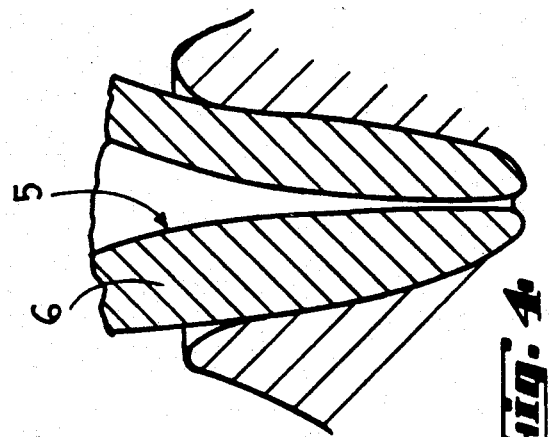
Fig. 4
| TYPE | N° | ∅ D1 | ∅ D2 |
|---|---|---|---|
| 15 | 1 | 0.15 | 0.47 |
| 15 | 2 | 0.15 | 0.52 |
| 15 | 3 | 0.15 | 0.57 |
| 20 | 1 | 0.20 | 0.52 |
| 20 | 2 | 0.20 | 0.57 |
| 20 | 3 | 0.20 | 0.62 |
| 25 | 1 | 0.25 | 0.57 |
| 25 | 2 | 0.25 | 0.62 |
| 25 | 3 | 0.25 | 0.67 |
| 30 | 1 | 0.30 | 0.62 |
| 30 | 2 | 0.30 | 0.67 |
| 30 | 3 | 0.30 | 0.72 |
| 35 | 1 | 0.35 | 0.67 |
| 35 | 2 | 0.35 | 0.72 |
| 35 | 3 | 0.35 | 0.77 |
| 40 | 1 | 0.40 | 0.72 |
| 40 | 2 | 0.40 | 0.77 |
| 40 | 3 | 0.40 | 0.82 |
Fig. 3

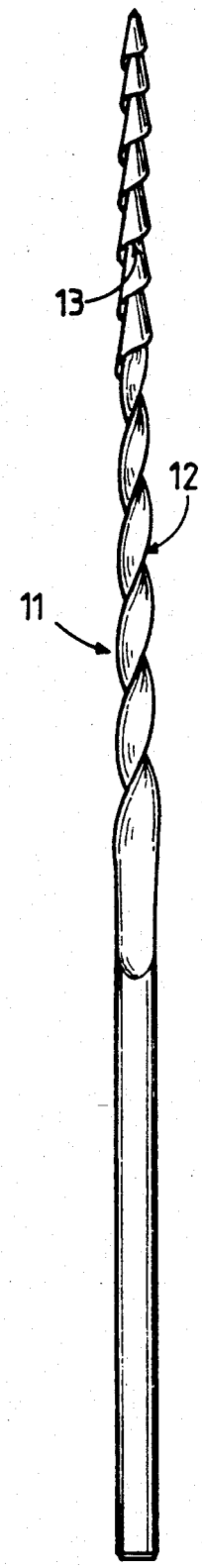

SET OF INSTRUMENTS FOR REAMING OUT DENTAL ROOT CANALS

BACKGROUND OF THE INVENTION 1.a) Field of the Invention

This invention relates to a set of instruments for reaming out dental root canals, each comprising a conical stem provided with at least a helicoidal cutting lip, and ending in a portion without said lip. The set furthermore comprises instruments the end diameters of which, that is to say the diameters measured at the roots of the end portions, are different from each other.

2.b) Description of the Prior Art

Such sets of instruments, constituted by reamers or files, are known per se.

The instrument sets are made in a series of different end diameters situated, most generally, between 0.06 mm and 1.4 mm. In these instruments, the conicity of the stem is constant, whatever the end diameter may be, this conicity being expressed, generally, not by the included angle, but by the difference between the end diameter and the diameter measured at the root of the helicoidal cutting lip or lips. The length of the portion of the stem provided with the said lip or lips being generally 16 mm, the difference between the end diameter and the diameter of the stem at the root of the lips is most generally about 0.32 mm.

The practitioner who executes reaming out of a dental root canal uses the instruments of the set, commencing with an instrument of small diameter and continuing, successively, with the instruments of increasing diameter until the whole infected dental pulp is eliminated and the canal reamed out has a shape suitable for its sealing by means of stopping with gutta-percha or cement.

The up to date odontological techniques instruct that the root canal should be given a more wide-mouthed shape than previously, the canal being large at its cervical portion near the crown of the tooth and remaining very narrow at its apical portion in the vicinity of the end of the dental root. As a matter of fact, this very wide-mouthed shape of the root canals after reaming out is more suitable for stopping by means of gutta-percha, a technique which is being used more and more.

SUMMARY OF THE INVENTION

The object of the present invention is to permit the realization of root canals reamed out so as to have more wide-mouthed shapes than was the case up to now.

This object is achieved by the fact that the set of instruments according to the invention comprises at least two instruments of the same diameter but the conicities of the stems of which are different.

The various features of the invention will be apparent from the following description, drawings and claims, the scope of the invention not being limited to the drawings themselves as the drawings are only for the purpose of illustrating ways in which the principles of the invention can be applied. Other embodiments of the invention utilizing the same or equivalent principles may be used and structural changes may be made as desired by those skilled in the art without departing from the present invention and the purview of the appended claims.

BRIEF DESCRIPTION OF THE DRAWINGS

FIG. 1 is a side view of an instrument for reaming out dental root canals.

FIG. 2 is a view of a detail of this instrument to an enlarged scale.

FIG. 3 is a table of the different instruments of a set in accordance with the invention, indicating the end diameters as well as the diameters at the root of helicoidal cutting lip or lips of the instruments.

FIG. 4 is a sectional view of a portion of a detal root showing the reamed-out canal which is obtained by means of the present set of instruments, and FIGS. 5, 6 and 7 are side views of three modifications of instruments for reaming out dental root canals.

DESCRIPTION OF THE PREFERRED EMBODIMENTS

The instrument as illustrated in FIG. 1 comprises a handle 1 in which is secured a conical stem 2 in the anterior portion of which are provided helicoidal cutting lips 3. In practice, the instrument will be manufactured from a tapered stem of polygonal section, for instance of square cross-section which will be subjected to a torsional deformation.

The end portion of the stem 2, which is without cutting lips, is constituted by a conical point 4 (FIG. 2). The diameter of the stem at the root of the point 4, which constitutes the nominal diameter employed as the identifying designation of the instrument as stated in the first column of the table of FIG. 3, is designated by D1, while the diameter at the root of the cutting lips 3 is designated by D2. The table of FIG. 3 shows that the instruments of the set are distributed in groups of three having the same end diameter D1, but of differing diameters D2.

Thus, in the first group indicated, of type "15", the instruments of which have a diameter D1 of 0.15 mm, the diameter D2 will be of 0.47, 0.52 and 0.57 mm, respectively, for each of the three instruments of the group. This represents a variation in the diameter D2 producing a corresponding variation of the included angle of the conicity of the stem 2.

The second group of three units, of the type "20", have a diameter D1 of 0.20 mm and diameters D2 of 0.52, 0.57 and 0.62 mm, respectively.

As shown by the table of FIG. 3, the diameters D1 vary, from one group to the next, of 0.05 of mm, the diameters D2 overlapping from one group to the next with the smallest diameter D2 of one group corresponding to the intermediary diameter D2 of the preceding group. Beyond a certain value of D1, for instance at and beyond 0.60 mm, the variation of D1, from one group to the next, will go for instance from 10 to 0.01 mm and not from 5 to 0.05 mm as for the smaller dimensions. The values of D2 will vary accordingly. The maximum diameter D1 will, normally, be of 1.40 mm, which will give diameters D2 of 1.62, 1.72 and 1.82 mm, respectively, for the three units of the last group.

The practitioner who desires to ream out a dental root canal, such as canal 5 provided in the root 6 (FIG. 4), giving it a wide-mouthed shape will use several groups of instruments of the set. Starting with a small dimension and increaing towards the greater dimensions, using successively the three units of each group of increasing dimension, before using the instruments of the next group.

In the example shown in FIG. 1, the handle 1 of the instrument is intended to be gripped by the practitioner between the thumb and the index finger. This enables a rotative or back-and-forth movement to be imparted to the instrument. But the invention can be applied as well to instruments adapted to be driven mechanically, the handle of such an instrument being arranged in such a way as to adapt itself to a handpiece of a driving machine.

Similarly, although the instrument illustrated has a conical point at its extremity without cutting lips, it could for example alternatively be ogival, round or flat, if desired.

In the modification of FIGS. 5 and 6, the instruments illustrated belong also to a set, as in the first embodiment, each of the instruments of these three modifications being however different from the corresponding one of FIG. 1.

The instrument of FIG. 5, generally designated by reference 7, distinguishes from that one of FIG. 1 mainly by the fact that its tapered portion is not conical but concave, as shown by the dot-and-dash line 8 which is the generating line of the surface of revolution within which tapered portion is inscribed.

The instrument of FIG. 6, generally designated by reference 9, distinguishes from that one of FIG. 1 by the fact that the pitch of the helicoidal cutting lips, designated by 10, decreases from the root of the tapered portion of the instrument towards the end point thereof.

Finally, in the modification of FIG. 7 the instrument, generally designated by reference 11, has its tapered portion which is provided with helicoidal cutting lips formed with a different shape at 12, in the vicinity of the root of the tapered portion, as compared with that at 13, adjacent the point of the instrument.

We claim:

1. A set of instruments for reaming out dental root canals, said set comprising, each instrument having a conical stem portion with at least one helicoidal cutting lip and a terminating end portion without said at least one lip, each instrument of said set having an end diameter measured at the root of said end portion, said set including at least two instruments having the same end diameter but different stem conicity, said set including several groups of instruments, each said group including a first, second and a third instrument, each instrument of any one group having a common end diameter, the conicities of the instruments of any one group differing from one to the other, wherein the conicities of the instruments overlap from one group to the next, the conicity of the second instrument of each group corresponding to the conicity of the instrument having the largest included angle of the immediately preceding group.

2. A set of instruments as claimed in claim 1 in which the included angle of the cone constituted by the stem of each instrument of any one of said groups varies from one instrument to the next one, in the same group.

* * * * *